(12) United States Patent
Kuroda et al.

(10) Patent No.: US 6,777,369 B1
(45) Date of Patent: Aug. 17, 2004

(54) PROCESS FOR PRODUCING CATALYST

(75) Inventors: Toru Kuroda, Hiroshima (JP); Seiichi Kawato, Hiroshima (JP); Masanori Nitta, Hiroshima (JP); Hideyasu Takezawa, Hiroshima (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 0 days.

(21) Appl. No.: 09/926,553
(22) PCT Filed: May 18, 2000
(86) PCT No.: PCT/JP00/03184
   § 371 (c)(1),
   (2), (4) Date: Nov. 19, 2001
(87) PCT Pub. No.: WO00/71248
   PCT Pub. Date: Nov. 30, 2000

(30) Foreign Application Priority Data

May 19, 1999 (JP) ........................................... 11-138770
Aug. 16, 1999 (JP) ........................................... 11-230058

(51) Int. Cl.$^7$ ........................... B01J 27/19; B01J 20/34; B01J 27/14; B32B 3/26; B01D 53/22
(52) U.S. Cl. ........................... 502/211; 502/22; 502/24; 502/25; 502/26; 502/54; 502/208; 502/209; 502/210; 502/212; 502/213; 502/514; 428/319.1; 428/312.8; 428/116; 96/4; 96/7; 96/11; 95/55; 95/56
(58) Field of Search ........................... 502/514, 54, 22, 502/24–26, 208–213; 428/319.1, 312.8, 116; 96/4, 7, 77; 95/55, 56

(56) References Cited

U.S. PATENT DOCUMENTS

| 4,165,296 A | * | 8/1979 | Ishii et al. ................... 252/412 |
| 4,419,267 A | * | 12/1983 | Sasaki et al. ................. 502/26 |
| 4,707,460 A | * | 11/1987 | Ishii et al. ..................... 502/26 |
| 4,814,305 A | * | 3/1989 | Kamogawa et al. .......... 502/26 |
| 5,250,485 A | * | 10/1993 | Kuroda et al. ............... 502/159 |
| 5,420,091 A | * | 5/1995 | Kuroda et al. ............... 502/209 |
| 5,422,326 A | * | 6/1995 | Kuroda et al. ............... 502/159 |
| 5,550,095 A | * | 8/1996 | Naito et al. ................. 502/211 |

FOREIGN PATENT DOCUMENTS

| GB | 2 029 719 | 3/1980 |
| JP | 54-2293 | 1/1979 |
| JP | 63-130144 | 6/1988 |

* cited by examiner

Primary Examiner—C. Melissa Koslow
Assistant Examiner—Patricia L. Hailey
(74) Attorney, Agent, or Firm—Oblon, Spivak, McClelland, Maier & Neustadt, P.C.

(57) ABSTRACT

The present invention relates to the effective utilization of a used catalyst containing at least molybdenum, an A element (at least one element selected from the group consisting of phosphorus and arsenic) and an X element (at least one element selected from the group consisting of potassium, rubidium and cesium), and provides a process for producing a catalyst, which comprises dispersing said used catalyst in water, adding thereto an alkali metal compound and/or ammonia solution, adjusting the resulting mixture to pH 6.5 or less to generate a precipitate containing at least molybdenum and the A element, and using the precipitate as a material for catalyst-constituting elements.

13 Claims, No Drawings

PROCESS FOR PRODUCING CATALYST

TECHNICAL FIELD

The present invention relates to a process for producing a catalyst using a compound recovered from a used catalyst, as a material for elements constituting the catalyst to be produced.

BACKGROUND ART

A catalyst containing at least molybdenum, an A element (at least one element selected from the group consisting of phosphorus and arsenic) and an X element (at least one element selected from the group consisting of potassium, rubidium and cesium) can be used for production of methacrylic acid by gas phase catalytic oxidation of methacrolein, production of methacrylic acid by oxidative dehydration of isobutyric acid, and other purpose.

In JP-A-53-113790 and JP-A-63-130144 are described processes for producing a catalyst using, as a material, a compound obtained by treating, with ammonia solution or the like, a used catalyst having a composition such as mentioned above, which used catalyst has been used for production of methacrylic acid by gas phase catalytic oxidation of methacrolein.

However, the catalysts produced by the processes described in JP-A-53-113790 and JP-A-63-130144 are different in structure from virgin catalysts produced by an ordinary process and therefore have shown low catalytic performances in some cases.

DISCLOSURE OF THE INVENTION

Hence, in order to effectively utilize a used catalyst containing at least molybdenum, an A element (at least one element selected from the group consisting of phosphorus and arsenic) and an X element (at least one element selected from the group consisting of potassium, rubidium and cesium), the present invention aims at providing a process for producing a catalyst using, as a material, a compound containing at least molybdenum and said A element, which has been recovered from a used catalyst having a composition such as mentioned above.

The gist of the present invention lies in a process for producing a catalyst, which comprises dispersing, in water, a used catalyst containing at least molybdenum, an A element (at least one element selected from the group consisting of phosphorus and arsenic) and an X element (at least one element selected from the group consisting of potassium, rubidium and cesium), adding thereto an alkali metal compound and/or ammonia solution, then adjusting the resulting mixture to pH 6.5 or less to generate a precipitate containing at least said molybdenum and said A element, and using the precipitate as a material for catalyst-constituting elements.

According to the present invention, it is possible to produce a catalyst using, as a material, a compound which has been recovered from a used catalyst containing at least molybdenum, an A element and an X element and which contains at least molybdenum and the A element; thereby, the used catalyst can be utilized effectively.

The present invention is particularly useful in producing a catalyst of a formula (1) (shown later) for production of methacrylic acid by gas phase catalytic oxidation of methacrolein, using a material recovered from a used catalyst which was, before the use, a catalyst of the formula (1) for production of methacrylic acid by gas phase catalytic oxidation of methacrolein.

According to the present invention, in recovering the compound containing at least molybdenum and the A element, molybdenum and the A element can be recovered at high ratios; therefore, the used catalyst can be utilized effectively.

BEST MODE FOR CARRYING OUT THE INVENTION

In the present invention, the used catalyst containing at least molybdenum, an A element and an X element includes catalysts which have been used in, for example, production of methacrylic acid by gas phase catalytic oxidation of methacrolein or production of methacrylic acid by oxidative dehydrogenation of isobutyric acid. A catalyst for use in production of methacrylic acid preferably has a composition represented by the following formula (1):

$$A_a Mo_b V_c Cu_d D_e X_f Y_g Z_h O_i \qquad (1)$$

(wherein Mo, V, Cu and O are molybdenum, vanadium, copper and oxygen, respectively; A is at least one element selected from the group consisting of phosphorus and arsenic; D is at least one element selected from the group consisting of antimony, bismuth, germanium, zirconium, tellurium, silver, selenium, silicon, tungsten and boron; X is at least one element selected from the group consisting of potassium, rubidium and cesium; Y is at least one element selected from the group consisting of iron, zinc, chromium, magnesium, tantalum, manganese, cobalt, barium, gallium, cerium and lanthanum; Z is sodium and/or thallium; a, b, c, d, e, f, g, h and i are each the atomic ratio of each element; when b is 12, a=0.5 to 3, c=0.01 to 3, d=0 to 2, e=0 to 3, f=0.01 to 3, g=0 to 3, h=0 to 3, and i is the atomic ratio of oxygen necessary for satisfying the valency of each component other than oxygen).

The used catalyst containing at least molybdenum, an A element and an X element is first dispersed in water. Thereto is added an alkali metal compound and/or ammonia solution. The amount of the alkali metal compound and/or ammonia solution added may be such that the molybdenum, A element and X element are dissolved; however, the amount is preferably such that the resulting mixture has a pH of 8 or more, more preferably such that the mixture has a pH of 8.5 to 12. The alkali metal compound usable has no particular restriction as to the kind; however, there can be mentioned, for example, sodium hydroxide, potassium hydroxide, cesium hydroxide and sodium hydrogencarbonate, with sodium hydroxide being preferred particularly.

Next, to the mixture after addition of the alkali metal compound and/or ammonia solution is added an acid for pH adjustment to 6.5 or less. It is preferable that, prior to the pH adjustment, the insolubles in the mixture are removed by filtration or the like. As the acid added for pH adjustment, there can be mentioned, for example, hydrochloric acid, nitric acid and sulfuric acid, with hydrochloric acid and nitric acid being preferred particularly.

The material after pH adjustment is preferably kept for a given time for formation of a precipitate. The time of keeping is preferably about 0.5 to 24 hours, and the liquid temperature is preferably about normal temperature to 90° C. During the keeping, the material may be allowed to stand but preferably is stirred.

The precipitate formed by pH adjustment, i.e. the compound containing at least molybdenum and an A element is presumed, from the compositional analysis and X-ray diffractometry, to contain, as the main component, a Dawson type heteropolyacid salt having a central element (e.g. phosphorus) and molybdenum ratio of 2:18, or a mixture of a Keggin type heteropolyacid salt having a central element (e.g. phosphorus) and molybdenum ratio of 1:12 and a Dawson type heteropolyacid. As the adjusted pH is lower, the proportion of the Keggin type heteropolyacid salt is larger.

When the proportion of each element contained in the precipitate formed from the used catalyst, relative to the amount of each element contained in the used catalyst is defined as the recovery of each element, the recovery of each element varies depending upon the composition of the used catalyst, the amount of ammonium root in the mixture before pH adjustment, and the adjusted pH. In the case of, for example, a used catalyst having a composition of the above-mentioned formula (1), the A element recovered in the form of a heteropolyacid salt of Keggin type is mostly phosphorus. Meanwhile, the A element recovered in the form of a heteropolyacid salt of Dawson type is phosphorus and arsenic; however, when both of them are present, arsenic is recovered preferentially. Therefore, in a used catalyst having a composition containing both phosphorus and arsenic, the adjustment of pH is preferably made to 1.5 or less in order to recover phosphorus preferentially, and to 2 to 6.5 in order to recover arsenic preferentially. In determining the pH to be adjusted, it is desirable to consider the recoveries of individual elements including molybdenum, etc.

In the present invention, the recovery of molybdenum can thus be made preferably 50 mass % or more, more preferably 70 mass % or more. Also, the recovery of the A element can be made preferably 50 mass % or more, more preferably 70 mass % or more.

When the amount of the X element is not sufficient to precipitate a heteropolyacid in the form of a salt of the X element, it is preferred that a raw material for ammonium root is added before the adjustment of pH so that the ammonium root is present in an amount of 0.5 mole or more, preferably 3 to 40 moles per mole of the A element. By this addition, a higher amount of a heteropolyacid can be precipitated in the form of an ammonium salt, and the molybdenum and the A element contained in the precipitate can be recovered at higher recoveries. A higher amount of the ammonium root results in higher recoveries of molybdenum and the A element. The kind of the ammonium root is not particularly restricted as long as it is soluble; and there can be mentioned, for example, ammonia solution, ammonium chloride, ammonium nitrate and ammonium carbonate.

The thus-precipitated compound contains molybdenum, the A element and, further, the X element. The presence of the X element in the compound is desirably a small amount or zero in some cases, depending upon the application of the compound. In such cases, the whole or part of the X element is preferably removed from the mixture before the pH adjustment to 6.5 or less.

There is no particular restriction as to the method for removing the X element. However, there can be mentioned, for example, a method of removing the X ion by its adsorption on an cation exchange resin. As the cation exchange resin, there can be used, for example, a styrene type resin and a chelate resin which are each an ordinary strongly acidic cation exchange resin, and a Na type ion exchange resin is preferred particularly. As to the timing of removal of the X element, there is no particular restriction as long as it is before the pH adjustment to 6.5 or less; however, removal of the X element is preferably made according to the following procedure.

That is, a used catalyst containing at least molybdenum, the A element and the X element is dispersed in water; thereto is added sodium hydroxide for dissolution; as necessary, the resulting insolubles are removed by filtration or the like; the X element is removed using a cation exchange resin or the like; a material for ammonium root is added in an amount of 0.5 mole or more per mole of the A element; then, an acid is added for pH adjustment to 6.5 or less.

There is no particular restriction as to the method for separating the precipitate formed by the pH adjustment, from the liquid containing the precipitate, and there can be mentioned ordinary methods such as filtration (e.g. gravity filtration, pressure filtration, vacuum filtration or filter press), centrifugation and the like. The precipitate may be washed as necessary in order to remove impurities from the precipitate. The solution for this washing is selected in view of the application and solubility of the precipitate, and there can be mentioned, for example, pure water and a dilute aqueous solution of ammonium nitrate, ammonium chloride or the like.

In the present invention, the thus-obtained precipitate is used as a material for catalyst. In this case, the state of the precipitate is not particularly restricted and may be a wet state or a dry state. Also, an oxide obtained by calcining the precipitate may be used when it is desired to use the material for catalyst in the form of an oxide. The calcination temperature is preferably 200 to 700° C.

In the present invention, the process for producing a catalyst is not particularly restricted and can be appropriately selected from various well known processes such as evaporation to dryness, precipitation, oxides mixing and the like, depending upon the state of the precipitate used as a material.

The catalyst produced in the present invention contains at least molybdenum, an A element and an X element. Meanwhile, an ordinary catalyst further on contains other elements so that the composition thereof is suitable for an intended reaction. For example, a catalyst used for production of methacrylic acid by gas phase catalytic oxidation of methacrolein, preferably has a composition of the previously-mentioned formula (1); in producing such a catalyst, materials other than the above-mentioned precipitate are also used. As such materials, there are mentioned oxides, nitrates, carbonates, ammonium salts, halides, etc. of the individual elements constituting the catalyst to be produced. As materials of, for example, molybdenum, there are mentioned ammonium paramolybdate, molybdenum trioxide, etc.

In producing a catalyst, there is first prepared a solution or aqueous slurry containing all materials for catalyst (the solution or slurry is hereinafter referred to as mixed solution). The mixed solution is subjected as necessary to drying, filtration, water content control by heating, or the like. The drying can be conducted by ordinary evaporation to dryness by heating, vacuum drying, air drying, or the like, and the temperature for drying is preferably 60 to 150° C.

Next, the thus-obtained mixed solution, water content-controlled mixed solution or dried material is shaped. The shaping in the present invention includes mechanical shaping using an ordinary powder molding machine such as tabletting machine, extrusion molding machine, tumbling granulator or the like; loading shaping of loading a catalyst component(s) on a carrier; drying shaping using a spray dryer, a drum dryer, a slurry dryer or the like; and so forth. There is no particular restriction as to the method for shaping.

The shape after shaping can be determined as desired, and it can be spherical, ring-shaped, columnar, hollow-spherical, flake-like, stellar, etc. As the carrier used in loading shaping, there can be mentioned, for example, inactive carriers such as silica, alumina, silica-alumina, magnesia, titania, silicon carbide and the like. An additive may be added in the shaping. Such an additive includes, for example, organic compounds such as polyvinyl alcohol, carboxymethyl cellulose and the like; inorganic compounds such as graphite, diatomaceous earth and the like; and inorganic fibers such as glass fiber, ceramic fiber, carbon fiber and the like.

The shaped catalyst is then subjected to a heat treatment. The conditions of the heat treatment are not particularly restricted and can be known treatment conditions. For example, in the case of a catalyst for production of methacrylic acid by gas phase catalytic oxidation of methacrolein, the temperature of the heat treatment is preferably 300 to 500° C. and it is preferred to conduct the heat treatment in an air stream or in a moisture-controlled air stream.

The catalyst produced according to the process of the present invention may be used by dilution with an inert carrier such as silica, alumina, silica-alumina, magnesia, titania, silicon carbide, stainless steel or the like.

When the catalyst produced according to the present process is used in a reaction, the reaction conditions are not particularly restricted and known reaction conditions can be used. Below are mentioned the reaction conditions when methacrylic acid is produced by gas phase catalytic oxidation of methacrolein.

The concentration of methacrolein in the raw material gas can be varied in a wide range but is preferably 1 to 20% by volume, particularly preferably 3 to 10% by volume. As the oxygen source in the raw material gas, air is economical and oxygen-enriched air may be used as necessary. The oxygen concentration in the raw material gas is preferably 0.3 to 4 moles, particularly preferably 0.4 to 2.5 moles per mole of methacrolein. The material gas may be diluted with an inert gas such as nitrogen, steam, carbon dioxide or the like. The reaction pressure may vary from normal pressure to several atm. The raw material gas may contain a small amount of impurities such as lower saturated aldehydes and the like, and these impurities gives substantially no adverse effect on the reaction. The reaction temperature can be selected in a range of 230 to 450° C., particularly preferably in a range of 250 to 400° C. The reaction may be conducted in a fixed bed or in a fluidized bed.

By conducting a reaction using a catalyst obtained by the production process of the present invention, it is possible to achieve a conversion which is preferably 90% or more, more preferably 95% or more of the conversion obtained using a virgin catalyst. It is also possible to achieve a selectivity which is preferably 90% or more, more preferably 95% or more of the selectivity obtained using a virgin catalyst. It is further possible to achieve a per-pass yield which is preferably 90% or more, more preferably 95% or more of the per-pass yield obtained using a virgin catalyst.

Hereinafter, the present invention is described using Examples. In the Examples, "part(s)" is/are. part(s) by mass; and the quantitative analyses of contained elements (or molecules) were made by ICP emission spectrometry, atomic absorption spectrometry, ion chromatography and Kjeldahl method. The quantitative analyses of raw material gas and product in production of methacrylic acid were made using gas chromatography. The recovery of each element, the conversion of methacrolein, and the selectivity and per-pass yield of methacrylic acid produced were calculated using the following formulas.

Recovery (%)=[(mass of element contained in obtained compound)/(mass of element contained in used catalyst)]×100

Conversion of methacrolein (%)=[(moles of reacted methacrolein)/(moles of fed methacrolein)]×100

Selectivity of methacrylic acid (%)=[(moles of produced methacrylic acid)/(moles of reacted methacrolein)]×100

Per-pass yield of methacrylic acid (%)=[(moles of produced methacrylic acid)/(moles of fed methacrolein)]×100

Reference Example 1

In 300 parts of pure water were dissolved, at 70° C., 63.62 parts of ammonium paramolybdate, 1.05 parts of ammonium metavanadate and 7.61 parts of cesium nitrate. Thereto was added a solution of 3.46 parts of 85 mass % phosphoric acid dissolved in 10 parts of pure water, followed by addition of 1.31 parts of antimony trioxide. The resulting mixture was heated to 95° C. with stirring. Then, a solution of 1.45 parts of copper nitrate dissolved in 10 parts of pure water was added, and the resulting mixture was evaporated to dryness with heating and stirring. The solid obtained was dried at 130° C. for 16 hours. The dried material was subjected to pressure molding, crushed, and sifted using a sieve to separate a moiety of 0.85 to 1.70 mm. It was heat-treated at 380° C. for 5 hours in an air stream to obtain a catalyst. This catalyst had a composition of $P_1Mo_{12}V_{0.3}Sb_{0.3}Cu_{0.2}Cs_{1.3}$.

The catalyst was charged into a reaction tube. Through the reaction tube was passed a mixed gas consisting of 5% by volume of methacrolein, 10% by volume of oxygen, 30% by volume of steam and 55% by volume of nitrogen, at a reaction temperature of 270° C. for a contact time of 3.6 seconds to conduct a reaction. As a result, the conversion of methacrolein was 80.8%, the selectivity of methacrylic acid was 81.2% and the per-pass yield of methacrylic acid was 65.6%.

EXAMPLE 1

In 400 parts of pure water was dispersed 87 parts of a used catalyst which had been used in a reaction for 2,000 hours under the same reaction conditions as in Reference Example 1 and which contained 34.54 parts of molybdenum, 0.93 part of phosphorus and 5.18 parts of cesium and had an oxygen-excluded composition (hereinafter, "composition" refers to an oxygen-excluded composition) of $P_1Mo_{12}Cs_{1.3}$. Thereto was added 68.2 parts of 25 mass % ammonia solution (ammonia root amount=2.77 moles per mole of molybdenum) and the resulting mixture was stirred for 1 hour. Thereto was added 107.1 parts of 36 mass % hydrochloric acid for pH adjustment to 2.0. The resulting solution was kept at 35° C. for 3 hours with stirring. The resulting precipitate was collected by filtration and washed with a 2 mass % ammonium nitrate solution to obtain a "recovered compound 1". The recovered compound 1 contained 34.19 parts of molybdenum, 0.93 part of phosphorus, 5.14 parts of cesium, and 0.19 mole, per mole of molybdenum, of ammonium root. The recoveries of individual elements were 99.0% (molybdenum), 100% (phosphorus) and 99.2% (cesium).

The recovered compound 1 was added to 250 parts of pure water. The resulting mixture was heated to 60° C. with stirring. Thereto were added, in the following order, a solution of 0.70 part of ammonium paramolybdate, 0.07 part of cesium nitrate and 13.57 parts of 25 mass % ammonia solution dissolved in 50 parts of pure water, 1.05 parts of ammonium metavanadate and 1.31 parts of antimony trioxide. The resulting mixture was heated to 95° C. with stirring.

Next, there were added a solution of 1.45 parts of copper nitrate dissolved in 10 parts of pure water and a solution of 3.10 parts of ammonium nitrate dissolved in 10 parts of pure water. The resulting mixture was evaporated to dryness with heating and stirring. The solid obtained was dried at 130° C. for 16 hours. The dried material was subjected to pressure molding, crushed and sifted using a sieve to separate a moiety of 0.85 to 1.70 mm. It was heat-treated at 380° C. for 5 hours in an air stream, to obtain a catalyst. The catalyst had the same composition as in Reference Example 1, i.e. $P_1Mo_{12}V_{0.3}Sb_{0.3}Cu_{0.2}Cs_{1.3}$.

A reaction was conducted using this catalyst under the same conditions as in Reference Example 1. As a result, the conversion of methacrolein was 80.7%, the selectivity of methacrylic acid was 81.5% and the per-pass yield of methacrylic acid was 65.8%. Thus, the catalyst had performances equal to those of the catalyst of Reference Example 1 produced by an ordinary process.

Reference Example 2

In 300 parts of pure water were dissolved, at 50° C., 63.62 parts of ammonium paramolybdate, 1.76 parts of ammonium metavanadate and 3.64 parts of potassium nitrate. Thereto was added a solution of 3.46 parts of 85 mass % phosphoric acid dissolved in 10 parts of pure water, followed by addition of a solution of 2.06 parts of gallium nitrate (Ga content=20.3% by mass) dissolved in 10 parts of pure water. The resulting mixture was heated to 95° C. Thereto were added, in the following order, a solution of 2.18 parts of copper nitrate dissolved in 10 parts of pure water, a solution of 0.93 part of boric acid dissolved in 10 parts of pure water and a solution of 1.72 parts of manganese nitrate dissolved in 10 parts of pure water. The resulting mixture was evaporated to dryness with heating and stirring. The solid obtained was dried at 130° C. for 16 hours. The dried material was subjected to pressure molding, crushed, and sifted using a sieve to separate a moiety of 0.85 to 1.70 mm. It was heat-treated at 380° C. for 5 hours in an air stream to obtain a catalyst. This catalyst had a composition of $P_1Mo_{12}V_{0.5}Cu_{0.3}Ga_{0.2}B_{0.5}Mn_{0.2}K_{1.2}$.

A reaction was conducted using this catalyst under the same conditions as in Reference Example 1. As a result, the conversion of methacrolein was 90.5%, the selectivity of methacrylic acid was 89.7% and the per-pass yield of methacrylic acid was 81.2%.

EXAMPLE 2

In 400 parts of pure water was dispersed 91 parts of a used catalyst which had been used in a reaction for 2,000 hours under the same reaction conditions as in Reference Example 1 and which contained 34.54 parts of molybdenum, 0.93 part of phosphorus, 1.41 parts of potassium, 0.76 part of vanadium and 0.57 part of copper and had a composition of $P_1Mo_{12}K_{1.2}V_{0.5}Cu_{0.3}$. Thereto was added 89.0 parts of a 45 mass % sodium hydroxide solution, and the resulting mixture was stirred for 1 hour. Then, the insolubles were removed by filtration. To the filtrate was added 127.2 parts of 36 mass % hydrochloric acid for pH adjustment to 1.0. The resulting solution was kept at 30° C. for 3 hours with stirring. The resulting precipitate was collected by filtration and washed with pure water to obtain a "recovered compound 2". The recovered compound 2 contained 20.72 parts of molybdenum, 0.52 part of phosphorus, 1.22 parts of potassium and 0.07 part of vanadium. The recoveries of individual elements were 60.0% (molybdenum), 55.9% (phosphorus), 86.5% (potassium) and 9.2% (vanadium).

In 300 parts of pure water were dissolved, at 50° C., 25.49 parts of ammonium paramolybdate, 1.60 parts of ammonium metavanadate and 0.49 part of potassium nitrate. To the solution being stirred was added the recovered compound 2. Then, a solution of 1.53 parts of 85 mass % phosphoric acid dissolved in 10 parts of pure water was added. Thereto was added 12.70 parts of 25 mass % ammonia solution, followed by addition of a solution of 2.06 parts of gallium nitrate (Ga content=20.3% by mass) dissolved in 10 parts of pure water. The resulting mixture was heated to 95° C. Subsequently, there were added, in the following order, a solution of 3.35 parts of copper nitrate dissolved in 30 parts of pure water, a solution of 0.93 part of boric acid dissolved in 10 parts of pure water, a solution of 1.72 parts of manganese nitrate dissolved in 10 parts of pure water and 31.2 parts of 6.1 mass % nitric acid. The resulting mixture was evaporated to dryness with heating and stirring. The solid obtained was dried at 130° C. for 16 hours. The dried material was subjected to pressure molding, crushed and sifted using a sieve to separate a moiety of 0.85 to 1.70 mm. It was heat-treated at 380° C. for 5 hours in an air stream, to obtain a catalyst. The catalyst had the same composition as in Reference Example 2, i.e. $P_1Mo_{12}V_{0.5}Cu_{0.3}Ga_{0.2}B_{0.5}Mn_{0.2}K_{1.2}$.

A reaction was conducted using this catalyst under the same conditions as in Reference Example 1. As a result, the conversion of methacrolein was 90.1%, the selectivity of methacrylic acid was 89.8% and the per-pass yield of methacrylic acid was 80.9%. Thus, the catalyst had performances equal to those of the catalyst of Reference Example 2 produced by an ordinary process.

Reference Example 3

To 400 parts of pure water were added 50.75 parts of molybdenum trioxide, 1.34 parts of vanadium pentoxide and 3.39 parts of 85 mass % phosphoric acid. The resulting mixture was stirred for 3 hours under refluxing. Thereto was added 0.70 part of copper oxide, followed by stirring for 2 hours under refluxing. The mixed solution after refluxing was cooled to 50° C. Thereto were added a solution of 3.56 parts of potassium nitrate dissolved in 20 parts of pure water and then a solution of 5 parts of ammonium nitrate dissolved in 20 parts of pure water. The resulting mixture was evaporated to dryness with heating and stirring. The solid obtained was dried at 130° C. for 16 hours. The dried material was subjected to pressure molding, crushed, and sifted using a sieve to separate a moiety of 0.85 to 1.70 mm. It was heat-treated at 370° C. for 3 hours in an air stream to obtain a catalyst. This catalyst had a composition of $P_1Mo_{12}V_{0.5}Cu_{0.3}K_{1.2}$.

A reaction was conducted using this catalyst under the same conditions as in Reference Example 1 except that the reaction temperature was 285° C. As a result, the conversion of methacrolein was 85.0%, the selectivity of methacrylic acid was 84.2% and the per-pass yield of methacrylic acid was 71.6%.

EXAMPLE 3

91 parts of the same used catalyst as in Example 2 was dispersed in 400 parts of pure water. Thereto was added 89.0 parts of a 45 mass % sodium hydroxide solution. The resulting mixture was stirred for 1 hour. The insolubles were removed by filtration. The filtrate was passed through a styrene type strongly acidic cation exchange resin made into a Na type, i.e. Amberlite IR-120B (a product of Organo Corporation), at SV=1 to remove potassium. To the solution after passing was added 29.1 parts of 36 mass % hydrochloric acid for pH adjustment to 8.9. Then, 19.25 parts of ammonium chloride (ammonium root amount=1.00 mole per mole of molybdenum) was added. Thereafter, 84.6 parts of 36 mass % hydrochloric acid was added for pH adjustment to 1.0. The resulting mixture was kept at 25° C. for 3 hours with stirring. The resulting precipitate was collected by filtration, washed with a 2 mass % ammonium nitrate solution, dried at 130° C. for 16 hours, and calcined at 400° C. for 5 hours in an air stream to obtain a "recovered compound 3". The recovered compound 3 contained 32.74 parts of molybdenum, 0.91 part of phosphorus and 0.67 part of vanadium. The recoveries of individual elements were 94.8% (molybdenum), 97.8% (phosphorus) and 88.2% (vanadium).

To 400 parts of pure water were added 1.63 pats of molybdenum trioxide, 0.14 part of vanadium pentoxide and the recovered compound 3. The resulting mixture was stirred for 3 hours under refluxing. Thereto was added 0.70 part of copper oxide, followed by stirring for 2 hours under refluxing. The mixed solution after refluxing was cooled to 50° C. Thereto were added a solution of 3.56 parts of potassium nitrate dissolved in 20 parts of pure water and further a solution of 5 parts of ammonium nitrate dissolved in 20 parts of pure water. The resulting mixture was evaporated to dryness with heating and stirring. The solid obtained was dried at 130° C. for 16 hours. The dried material was subjected to pressure molding, crushed and sifted using a sieve to separate a moiety of 0.85 to 1.70 mm. It was heat-treated at 370° C. for 3 hours in an air stream, to obtain a catalyst. The catalyst had the same composition as in Reference Example 3, i.e. $P_1Mo_{12}V_{0.5}Cu_{0.3}K_{1.2}$.

A reaction was conducted using this catalyst under the same conditions as in Reference Example 3. As a result, the conversion of methacrolein was 84.9%, the selectivity of methacrylic acid was 84.8% and the per-pass yield of methacrylic acid was 72.0%. Thus, the catalyst had performances equal to those of the catalyst of Reference Example 3 produced by an ordinary process.

Reference Example 4

In 300 parts of pure water were dissolved, at 60° C., 63.52 parts of ammonium paramolybdate, 1.05 parts of ammonium metavanadate and 7.60 parts of cesium nitrate. To the solution being stirred was added a solution of 3.46 parts of 85 mass % phosphoric acid and 3.55 parts of 60 mass % arsenic acid dissolved in 20 parts of pure water. Further, 0.63 part of germanium dioxide was added. The resulting mixture was heated to 95° C. Then, a solution of 1.78 parts of zinc nitrate dissolved in 10 parts of pure water was added. The resulting mixture was evaporated to dryness with heating and stirring. The solid obtained was dried at 130° C. for 16 hours. The dried material was subjected to pressure molding, crushed, and sifted using a sieve to separate a moiety of 0.85 to 1.70 mm. It was heat-treated at 380° C. for 5 hours in an air stream to obtain a catalyst. This catalyst had a composition of $P_1Mo_{12}V_{0.3}As_{0.5}Ge_{0.2}Zn_{0.2}Cs_{1.3}$.

A reaction was conducted using this catalyst under the same conditions as in Reference Example 1 except that the reaction temperature was 290° C. As a result, the conversion of methacrolein was 85.3%, the selectivity of methacrylic acid was 85.2% and the per-pass yield of methacrylic acid was 72.7%.

EXAMPLE 4

In 400 parts of pure water was dispersed 89 parts of a used catalyst which had been used in a reaction for 2,000 hours under the same reaction conditions as in Reference Example 1 and which contained 34.54 parts of molybdenum, 0.93 part of phosphorus, 5.18 parts of cesium and 1.12 parts of arsenic and had a composition of $P_1Mo_{12}As_{0.5}Cs_{1.3}$. Thereto was added 89.0 parts of a 45 mass % sodium hydroxide solution, followed by stirring for 1 hour. Thereto was added 32.5 parts of 36 mass % hydrochloric acid for pH adjustment to 7.5. Thereto was added 28.90 parts of ammonium chloride (ammonium root amount=1.50 moles per mole of molybdenum), followed by addition of 55.6 parts of 36 mass % hydrochloric acid for pH adjustment to 4.0. The resulting mixture was kept at 30° C. for 3 hours with stirring. The resulting precipitate was collected by filtration and washed with a 2 mass % ammonium nitrate solution to obtain a "recovered compound 4". The recovered compound 4 contained 23.94 parts of molybdenum, 0.48 part of phosphorus, 5.14 parts of cesium, 1.12 parts of arsenic and 0.48 mole, per mole of molybdenum, of ammonium root. The recoveries of individual elements were 69.3% (molybdenum), 51.6% (phosphorus), 99.2% (cesium) and 100% (arsenic).

In 300 parts of pure water were dissolved, at 60° C., 19.46 parts of ammonium paramolybdate, 1.05 parts of ammonium metavanadate and 0.06 part of cesium nitrate. To the solution being stirred was added the recovered compound 4. Then, a solution of 1.67 parts of 85 mass % phosphoric acid dissolved in 10 parts of pure water was added. Thereto was added 6.41 parts of 25 mass % ammonia solution, followed by addition of 0.63 part of germanium dioxide. The resulting mixture was heated to 95° C. Then, there were added a solution of 1.78 parts of zinc nitrate dissolved in 10 parts of pure water and 39.9 parts of 6.1 mass % nitric acid. The resulting mixture was evaporated to dryness with heating and stirring. The solid obtained was dried at 130° C. for 16 hours. The dried material was subjected to pressure molding, crushed and sifted using a sieve to separate a moiety of 0.85 to 1.70 mm. It was heat-treated at 380° C. for 5 hours in an air stream, to obtain a catalyst. The catalyst had the same composition as in Reference Example 4, i.e. $P_1Mo_{12}V_{0.3}As_{0.5}Ge_{0.2}Zn_{0.2}Cs_{1.3}$.

A reaction was conducted using this catalyst under the same conditions as in Reference Example 4. As a result, the conversion of methacrolein was 85.3%, the selectivity of methacrylic acid was 85.5% and the per-pass yield of methacrylic acid was 72.9%. Thus, the catalyst had performances equal to those of the catalyst of Reference Example 4 produced by an ordinary process.

Reference Example 5

63.52 parts of ammonium paramolybdate was dissolved in 300 parts of pure water at 60° C. To the solution being stirred were added,. in the following order, a solution of 3.46 parts of 85 mass % phosphoric acid dissolved in 10 parts of pure water and a solution of 3.55 parts of 60 mass % arsenic acid dissolved in 10 parts of pure water. Thereto were added, in the following order, a solution of 2.17 parts of copper nitrate dissolved in 10 parts of pure water and 1.75 parts of ammonium metavanadate. Thereto was added a solution of 3.64 parts of potassium nitrate dissolved in 20 parts of pure water. The resulting material was evaporated to dryness with heating and stirring. The solid obtained was dried at 130° C. for 16 hours. The dried material was subjected to pressure molding, crushed, and sifted using a sieve to separate a moiety of 0.85 to 1.70 mm. It was heat-treated at 380° C. for 5 hours in an air stream to obtain a catalyst. This catalyst had a composition of $P_1Mo_{12}V_{0.5}As_{0.5}Cu_{0.3}K_{1.2}$.

A reaction was conducted using this catalyst under the same conditions as in Reference Example 1 except that the reaction temperature was 300° C. As a result, the conversion of methacrolein was 82.4%, the selectivity of methacrylic acid was 86.9% and the per-pass yield of methacrylic acid was 71.6%.

EXAMPLE 5

In 400 parts of pure water was dispersed 94 parts of a used catalyst which had been used in a reaction for 2,000 hours under the same reaction conditions as in Reference Example 1 and which contained 34.54 parts of molybdenum, 0.93 part of phosphorus, 1.41 parts of potassium, 0.76 part of vanadium, 0.57 part of copper and 1.12 parts of arsenic and had a composition of $P_1Mo_{12}V_{0.5}As_{0.5}Cu_{0.3}K_{1.2}$. Thereto was added 89.0 parts of a 45 mass % sodium hydroxide solution, followed by stirring for 1 hour. The insolubles were removed by filtration. To the filtrate was added 29.6 parts of 36 mass % hydrochloric acid for pH adjustment to 9.0. Thereto was added 28.90 parts of ammonium chloride (ammonium a root amount=1.50 moles per mole of molybdenum), followed by addition of 48.4 parts of 36 mass % hydrochloric acid for pH adjustment to 5.0. The resulting mixture was kept at 60° C. for 3 hours with stirring. The resulting precipitate was collected by filtration and washed with a 2 mass % ammonium nitrate solution to obtain a "recovered compound 5". The recovered compound 5 contained 25.97 parts of molybdenum, 0.56 part of phosphorus, 0.57 part of potassium, 0.38 part of vanadium, 1.12 parts of arsenic and 0.58 mole, per mole of molybdenum, of ammonium root. The recoveries of individual elements were 75.2% (molybdenum), 60.2% (phosphorus), 40.4% (potassium), 50.0% (vanadium) and 100% (arsenic). 15.73 parts of ammonium paramolybdate was dissolved in 300 parts of pure water at 60° C. To the solution being stirred were added a solution of 1.37 parts of 85 mass % phosphoric acid dissolved in 10 parts of pure water, 4.63 parts of 25 mass % ammonia solution and the recovered compound 5. Then, there were added, in the following order, a solution of 2.17 parts of copper nitrate dissolved in 10 parts of pure water and 0.88 part of ammonium metavanadate. Thereto were added a solution of 2.16 parts of potassium nitrate dissolved in 20 parts of pure water and a solution of 1.17 parts of ammonium nitrate dissolved in 10 parts of pure water. The resulting mixture was evaporated to dryness with heating and stirring. The solid obtained was dried at 130° C. for 16 hours. The dried material was subjected to pressure molding, crushed and sifted using a sieve to separate a moiety of 0.85 to 1.70 mm. It was heat-treated at 380° C. for 5 hours in an air stream, to obtain a catalyst. The catalyst had the same composition as in Reference Example 5, i.e. $P_1Mo_{12}V_{0.5}As_{0.5}Cu_{0.3}K_{1.2}$.

A reaction was conducted using this catalyst under the same conditions as in Reference Example 5. As a result, the conversion of methacrolein was 81.8%, the selectivity of methacrylic acid was 87.3% and the per-pass yield of methacrylic acid was 71.4%. Thus, the catalyst had performances equal to those of the catalyst of Reference Example 5 produced by an ordinary process.

Reference Example 6

In 200 parts of pure water were dissolved, at 70° C., 63.52 parts of ammonium paramolybdate, 1.75 parts of ammonium metavanadate and 7.60 parts of cesium nitrate. To the solution being stirred was added a solution of 3.55 parts of 60 mass % arsenic acid dissolved in 10 parts of pure water. Thereto was added a solution of 3.46 parts of 85 mass % phosphoric acid dissolved in 10 parts of pure water, and the resulting mixture was heated to 95° C. Thereto were added, in the following order, a solution of 2.17 parts of copper nitrate dissolved in 10 parts of pure water and a solution of 2.60 parts of cerium nitrate and 1.30 parts of lanthanum nitrate dissolved in 20 parts of pure water. The resulting mixture was evaporated to dryness with heating and stirring. The solid obtained was dried at 130° C. for 16 hours. The dried material was subjected to pressure molding, crushed, and sifted using a sieve to separate a moiety of 0.85 to 1.70 mm. It was heat-treated at 380° C. for 5 hours in an air stream to obtain a catalyst. This catalyst had a composition of $P_1Mo_{12}V_{0.5}As_{0.5}Cu_{0.3}Ce_{0.2}La_{0.1}Cs_{1.3}$.

A reaction was conducted using this catalyst under the same conditions as in Reference Example 1. As a result, the conversion of methacrolein was 89.8%, the selectivity of methacrylic acid was 87.6% and the per-pass yield of methacrylic acid was 78.7%.

EXAMPLE 6

94 parts of the same used catalyst as in Example 5 was dispersed in 400 parts of pure water. Thereto was added 89.0 parts of a 45 mass % sodium hydroxide solution, followed by stirring for 1 hour. The insolubles were removed by filtration. The filtrate was passed through a Na type chelate resin, Lewatitt TP 207 (a product of Bayer Co.) at SV=1 to remove potassium. To the solution after passing was added 27.1 parts of 36 mass % hydrochloric acid for pH adjustment to 8.5. Then, 28.90 parts of ammonium chloride (ammonium root amount=1.50 moles per mole of molybdenum) was added. Thereafter, 51.5 parts of 36 mass % hydrochloric acid was added for pH adjustment to 5.0. The resulting mixture was kept at 30° C. for 3 hours with stirring. The resulting precipitate was collected by filtration and washed with a 2 mass % ammonium nitrate solution to obtain a "recovered compound 6". The recovered compound 6 contained 24.52 parts of molybdenum, 0.51 part of phosphorus, 0.33 part of vanadium, 1.12 parts of arsenic and 0.64 mole, per mole of molybdenum, of ammonium root. The recoveries of individual elements were 71.0% (molybdenum), 54.8% (phosphorus), 43.4% (vanadium) and 100% (arsenic).

In 300 parts of pure water were dissolved, at 70° C., 18.39 parts of ammonium paramolybdate, 1.00 part of ammonium metavanadate and 7.60 parts of cesium nitrate. To the solution being stirred was added the recovered compound 6. Then, a solution of 1.56 parts of 85 mass % phosphoric acid dissolved in 10 parts of pure water. Thereto was added 4.22 parts of 25 mass % ammonia solution. The resulting mixture was heated to 95° C. Thereto were added, in the following order, a solution of 2.17 parts of copper nitrate dissolved in 10 parts of pure water and a solution of 2.60 parts of cerium nitrate and 1.30 parts of lanthanum nitrate dissolved in 20 parts of pure water. The resulting mixture was evaporated to dryness with heating and stirring. The solid obtained was dried at 130° C. for 16 hours. The dried material was subjected to pressure molding, crushed and sifted using a sieve to separate a moiety of 0.85 to 1.70 mm. It was heat-treated at 380° C. for 5 hours in an air stream, to obtain a catalyst. The catalyst had the same composition as in Reference Example 6, i.e. $P_1Mo_{12}V_{0.5}As_{0.5}Cu_{0.3}Ce_{0.2}La_{0.1}Cs_{1.3}$.

A reaction was conducted using this catalyst under the same conditions as in Reference Example 6. As a result, the conversion of methacrolein was 89.6%, the selectivity of methacrylic acid was 88.2% and the per-pass yield of methacrylic acid was 79.0%. Thus, the catalyst had performances equal to those of the catalyst of Reference Example 6 produced by an ordinary process.

What is claimed is:

1. A process for producing a catalyst, which comprises dispersing, in water, a used catalyst containing at least molybdenum, an A element (at least one element selected from the group consisting of phosphorus and arsenic) and an X element (at least one element selected from the group consisting of potassium, rubidium and cesium), adding thereto an alkali metal compound and/or ammonia solution so as to adjust the resulting mixture to pH 8 or more, then adding thereto an acid so as to adjust the resulting mixture to pH 6.5 or less to generate a precipitate containing at least said molybdenum and said A element, separating the precipitate from the liquid containing the precipitate, and forming a catalyst from the precipitate as a source material for said catalyst.

2. A process for producing a catalyst according to claim 1, wherein the mixture before adjustment to pH 6.5 or less has an ammonium root in an amount of 0.5 mole or more relative to mole of the A element.

3. A process for producing a catalyst according to claim 1, wherein the whole or part of the X element is removed from the mixture before adjustment to pH 6.5 or less.

4. A process for producing a catalyst according to claim 1, wherein the precipitate is heat-treated at 200 to 700° C. and then used as said source material.

5. A process for producing a catalyst according to claim 1, wherein the used catalyst was, before the use, a catalyst for production of methacrylic acid by gas phase catalytic oxidation of methacrolein, having a composition represented by the following formula (1):

$$A_a Mo_b V_c Cu_d D_e X_f Y_g Z_h O_i \quad (1)$$

(wherein Mo, V, Cu and O are molybdenum, vanadium, copper and oxygen, respectively; A is at least one element selected from the group consisting of phosphorus and arsenic; D is at least one element selected from the group consisting of antimony, bismuth, germanium, zirconium, tellurium, silver, selenium, silicon, tungsten and boron; X is at least one element selected from the group consisting of potassium, rubidium and cesium; Y is at least one element selected from the group consisting of iron, zinc, chromium, magnesium, tantalum, manganese, cobalt, barium, gallium, cerium and lanthanum; Z is sodium and/or thallium; a, b, c, d, e, f, g, h and i are each the atomic ratio of each element; when b is 12, a=0.5 to 3, c=0.01 to 3, d=0 to 2, e=0 to 3, f=0.01 to 3, g=0 to 3, h=0 to 3, and i is the atomic ratio of oxygen necessary for satisfying the valency of each component other than oxygen).

6. A process for producing a catalyst according to claim 5, wherein the mixture before adjustment to pH 6.5 or less has an ammonium root in an amount of 0.5 mole or more relative to mole of the A element.

7. A process for producing a catalyst according to claim 5, wherein the whole or part of the X element is removed from the mixture before adjustment to pH 6.5 or less.

8. A process for producing a catalyst according to claim 5, wherein the produced catalyst is a catalyst for production of methacrylic acid by gas phase catalytic oxidation of methacrolein, having a composition represented by the formula (1).

9. A process for producing a catalyst according to claim 8, wherein the produced catalyst gives a conversion of 90% or more relative to that of a virgin catalyst, a selectivity of 90% or more relative to that of the virgin catalyst and a per-pass yield of 90% or more relative to that of the virgin catalyst.

10. A process for producing a catalyst according to claim 1, wherein the produced catalyst is a catalyst for production of methacrylic acid by gas phase catalytic oxidation of methacrolein, having a composition represented by the following formula (1):

$$A_a Mo_b V_c Cu_d D_e X_f Y_g Z_h O_i \quad (1)$$

(wherein Mo, V, Cu and O are molybdenum, vanadium, copper and oxygen, respectively; A is at least one element selected from the group consisting of phosphorus and arsenic; D is at least one element selected from the group consisting of antimony, bismuth, germanium, zirconium, tellurium, silver, selenium, silicon, tungsten and boron; X is at least one element selected from the group consisting of potassium, rubidium and cesium; Y is at least one element selected from the group consisting of iron, zinc, chromium, magnesium, tantalum, manganese, cobalt, barium, gallium, cerium and lanthanum; Z is sodium and/or thallium; a, b, c, d, e, f, g, h and i are each the atomic ratio of each element; when b is 12, a=0.5 to 3, c=0.01 to 3, d=0 to 2, e=0 to 3, f=0.01 to 3, g=0 to 3, h=0 to 3, and i is the atomic ratio of oxygen necessary for satisfying the valency of each component other than oxygen).

11. A process for producing a catalyst according to claim 1, wherein the recovery of molybdenum is 50 mass % or more and the recovery of the A element is 50 mass % or more.

12. A process for producing a catalyst according to claim 1, wherein the precipitate contains, as the main component, at least one selected from the group consisting of a salt of an X element of a Dawson type heteropolyacid containing at least molybdenum and an A element, an ammonium salt of a Dawson type heteropolyacid containing at least molybdenum and an A element, a salt of an X element of a Keggin type heteropolyacid containing at least molybdenum and an A element, and an ammonium salt of a Keggin type heteropolyacid containing at least molybdenum and an A element.

13. A process for producing a catalyst according to claim 1, wherein a material other than the precipitate is used as a source material with the precipitate in forming the catalyst.

* * * * *